United States Patent
Cheng et al.

(10) Patent No.: US 7,566,556 B2
(45) Date of Patent: Jul. 28, 2009

(54) ENHANCING ENZYME THERMOSTABILITY BY MIXING WITH SORGHUM LIQUOR WASTE

(75) Inventors: Kou-Joan Cheng, Richmond (CA); Ching-Tsan Huang, Taipei (TW); Chang-Chih Chen, Taipei (TW)

(73) Assignee: Academia Sinica, Taipei (TW)

( * ) Notice: Subject to any disclaimer, the term of this patent is extended or adjusted under 35 U.S.C. 154(b) by 609 days.

(21) Appl. No.: 10/087,699

(22) Filed: Mar. 1, 2002

(65) Prior Publication Data

US 2003/0166195 A1 Sep. 4, 2003

(51) Int. Cl.
*C12N 9/96* (2006.01)
*C12N 9/14* (2006.01)
*C12N 9/16* (2006.01)
*C12N 9/24* (2006.01)
*C12N 9/26* (2006.01)
*C12N 9/42* (2006.01)

(52) U.S. Cl. ............... 435/188; 435/195; 435/196; 435/200; 435/201; 435/209

(58) Field of Classification Search ........... 435/183, 435/187, 188, 195
See application file for complete search history.

(56) References Cited

U.S. PATENT DOCUMENTS

| | | | | |
|---|---|---|---|---|
| 2,529,131 A * | 11/1950 | Firmin et al. | ............... | 435/162 |
| 3,983,255 A * | 9/1976 | Bass | ............... | 426/54 |
| 4,077,842 A * | 3/1978 | Cory et al. | ............... | 435/188 |
| 4,320,151 A * | 3/1982 | Cole | ............... | 426/18 |
| 4,337,123 A * | 6/1982 | De Sa et al. | ............... | 203/19 |
| 4,415,656 A * | 11/1983 | Rohrbach et al. | ............... | 435/96 |
| 4,613,339 A * | 9/1986 | Gunnerman et al. | ............... | 422/40 |
| 4,661,287 A * | 4/1987 | Crossin | ............... | 510/300 |
| 5,108,746 A * | 4/1992 | Rho et al. | ............... | 424/94.2 |
| 5,730,877 A * | 3/1998 | Heikkila et al. | ............... | 210/659 |
| 6,132,716 A * | 10/2000 | Morgan et al. | ............... | 424/94.61 |
| 6,294,365 B1 * | 9/2001 | De Rosier et al. | ............... | 435/188 |
| 6,558,693 B1 * | 5/2003 | Knap et al. | ............... | 424/442 |

OTHER PUBLICATIONS

Chang-Chuh Chen, et al. *Improvement of phytase thermostability by using sorghum liquor wastes supplemented with starch.* Biotechnology Letters, vol. 23, 2001, pp. 331-333.

Pedro Lamosa, et al. *Thermostabilization of Proteins by Diglycerol Phosphate, a New Compatible Solute from the Hyperthermophile Archaeoglobus fulgidus.* Applied and Environmental Microbiology, vol. 66, No. 5, May 2000, pp. 1974-1979.

Sandeep Kumar, et al. *Factors enhancing protein thermostability.* Protein Engineering, vol. 13, No. 3, 2000, pp. 179-191.

* cited by examiner

*Primary Examiner*—David M Naff
(74) *Attorney, Agent, or Firm*—Occhiuti Rohlicek & Tsao LLP

(57) ABSTRACT

A composition containing a thermolabile protein admixed with a liquor waste. Also disclosed is a method of preparing such a composition which contains a protein with enhanced thermostability.

9 Claims, No Drawings

ENHANCING ENZYME THERMOSTABILITY BY MIXING WITH SORGHUM LIQUOR WASTE

BACKGROUND

Thermostability of proteins, especially enzymes, is very important in industrial applications that involve high temperature processes. Three generic approaches have been taken to make proteins more stable under high temperature conditions: (1) screening naturally-occurring proteins with thermostable properties; (2) using molecular biology techniques to modify, and thus improve the thermostability of, natural proteins; and (3) employing additives to protect proteins from high temperatures.

SUMMARY

The present invention relates to a method of enhancing protein thermostability. The method includes mixing a solution of a thermolabile protein (e.g., an enzyme) with a liquor waste, and drying the mixture. Examples of a liquor waste include a crop liquor waste such as a white liquor waste (e.g., a sorghum liquor waste). The liquor waste, preferably distilled, may be dried before being mixed with a protein solution.

Also within the scope of this invention is a composition containing a thermolabile protein admixed with a liquor waste. The protein in such a composition has enhanced thermostability. In other words, as a result of its interactions with the liquor waste, the protein becomes more stable at high temperatures.

The present invention provides an easy, safe, and low-cost method for enhancing protein thermostability. The details of one or more embodiments of the invention are set forth in the accompanying description below. Other features, objects, and advantages of the invention will be apparent from the description, and from the claims.

DETAILED DESCRIPTION

This invention is based on the discovery that a liquor waste can be used to improve protein thermostability. Specifically, when a protein solution is completely mixed with a liquor waste to homogeneity, the stability of the protein is increased.

The liquor waste may be distilled (e.g., doubly distilled). It can be dried (e.g., at 60° C. for 24 h) and grounded and sieved (e.g., with a net of 0.64-cm mesh) before it is mixed with a protein solution.

The thermolabile protein can be a heat-sensitive enzyme, or any other heat-sensitive protein. The optimal ratio (v/w) at which a protein solution is mixed with a liquor waste can be determined according to the methods described in the examples below or by any other applicable methods.

The protein-liquor waste mixture can be dried (e.g., at 50° C.) to facilitate transportation and long-term storage. The drying temperature varies from protein to protein, depending on the thermostability of the protein.

Unexpectedly a thermolabile protein is more stable at high temperatures in a protein-liquor waste composition described above. For example, when a phytase solution is mixed with a dried sorghum liquor waste at a ratio of 1:10 (v/w), more than 90% of the phytase activity remains after treatment at 60° C. for 30 min. By contrast, all activity is lost for phytase treated in the same manner in the absence of a sorghum liquor waste. Furthermore, the phytase activity remains after long-term storage (e.g., 180 days) at room temperature.

The present invention is very useful in industrial applications that involve high temperature processes, for instance, the pelleting procedure routinely used in the feed, food, and pharmaceutical industry. With improved thermostability, a protein is able to retain its activity at high processing temperatures.

As shown in the examples below, a sorghum liquor waste can be used to improve the thermostability of phytase, cellulase and α-Amylase. As the sorghum liquor waste is generally regarded as safe and can be obtained on a large scale at low costs, the method and composition of this invention are particularly useful in the feed and food industry in which these three enzymes are major additives.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

EXAMPLES

Example 1

Increasing Phytase Thermostability with Sorghum Liquor Waste

A sorghum liquor waste was prepared as the remains after two distillations of fermented sorghum. The major composition of a sorghum liquor waste was crude starch (10-13%), crude proteins (14-22%), crude lipids (4-7%), crude fibers (17-21%), and ash (4-46%). The sorghum liquor waste was dried at 60° C. for 24 h, then grounded and sieved with a net of 0.64-cm mesh before use.

Phytase was extracted from 1 g BASF Natuphos powder (5,000 U/g) using 4 ml 100 mM sodium acetate buffer (pH 5.0). Phytase solution (c.a. 1250 U/ml) was obtained by collecting the supernatant after centrifugation at 12,400 g for 10 min. One ml of phytase solution was added into 1-10 g sorghum liquor waste and mixed completely. The phytase-sorghum liquor waste mixtures were dried in an oven at 50° C. for 1 h. After drying, the phytase-sorghum liquor waste mixtures were incubated at 37, 50, 60, 70, 80, or 90° C. for 30 min. The phytase-sorghum liquor waste mixtures were then extracted with a 100 mM acetate buffer (pH 5.0). Phytase activity was assayed according to Bae et al. (1999) J. Microbiol. Methods 39: 17-22, and the absorbance at 700 nm was recorded. One unit of phytase activity was defined as the amount of activity that releases 1 μmol of phosphate per minute at 37° C.

In the absence of the sorghum liquor waste, about 75% and 40% of the phytase activity remained after 30 min of treatment at 50 and 55° C., respectively. No phytase activity was detected after exposure to 60° C. for 30 min. Unexpectedly, when phytase was mixed with the sorghum liquor waste at a ratio of 1:2 (v/w), about 90% of the phytase activity remained after the 55° C. treatment, and 70% activity remained after the 60° C. treatment. When phytase was mixed with the sorghum liquor waste at a ratio of 1:10 (v/w), more than 90% of phytase activity remained after the treatment at 50, 60 or 70° C., 55% of activity was detected at 80° C., and over 20% of activity was recovered at 90° C.

Example 2

Increasing Cellulase Thermostability with Sorghum Liquor Waste

A sorghum liquor waste was prepared following the procedure described in Example 1.

Cellulase was purchased from Sigma Chemical Company (St. Louis, Mo., U.S.A.; C1184). A cellulase solution (c.a. 20 U/ml) was obtained by dissolving 450 mg cellulase in 10 ml of 50 mM sodium citrate (pH 4.8). One ml of the cellulase solution was added into 1 or 10 g sorghum liquor waste and mixed completely. The cellulase-sorghum liquor waste mixtures were dried in an oven at 50° C. for 1 h. After drying, the cellulase-sorghum liquor waste mixtures were incubated at 37, 50, 60, 70, 80, or 90° C. for 30 min. The cellulase-sorghum liquor waste mixtures were then extracted with a 50 mM sodium citrate buffer (pH 4.8). Cellulase activity was determined by measuring the amount of reducing sugars released from 0.5% carboxymethylcellulose in a 50 mM sodium citrate buffer (pH 4.8) using the dinitrosalicylic acid method (Wood and Bhat (1988) Methods in Enzymology 160: 87-143). A standard curve was generated using glucose as the standard at pH 4.8 and 37° C. One unit of cellulase activity was defined as the amount of activity that produces 1 μmol of reducing sugars per min at 37° C.

More than 95% of the cellulase activity remained after 30 min of treatment at 50, 60 or 70° C. in the absence of the sorghum liquor waste. Only 20% of the activity left after treatment at 80° C. for 30 min, and no cellulase activity was detected after exposure to 90° C. for 30 min. Unexpectedly, when cellulase was mixed with the sorghum liquor waste at a ratio of 1:10 (v/w), almost no activity was lost after 30 min treatment at 50, 60, 70 or 80° C. More than 80% of the cellulase activity remained after the 90° C. treatment, and 70% activity remained even after treatment at 100° C.

Example 3

Increasing α-Amylase Thermostability with Sorghum Liquor Waste

A sorghum liquor waste was prepared following the procedure described in Example 1.

α-Amylase (1,000 U/ml) was purchased from Megazyme International Irland Ltd. (Bray Co., Wicklow, Irland; E-ANAAM). One ml of the α-amylase solution was added into 10 g sorghum liquor waste and mixed completely. The α-amylase-sorghum liquor waste mixtures were dried in an oven at 50° C. for 1 h. After drying, the α-amylase-sorghum liquor waste mixtures were incubated at 37, 50, 60, 70, 80, or 90° C. for 10 min. The α-amylase-sorghum liquor waste mixtures were then extracted with a 60 mM phosphate buffer (pH 7.0). α-amylase activity was determined by measuring the amount of reducing sugars released from 0.7% starch (Sigma) in a 60 mM phosphate buffer (pH 7.0). 0.2 ml reaction mixture containing the enzyme and the substrate in the buffer system was incubated at 37° C. for 10 min. The reaction was terminated by adding 0.1 ml of stop solution (25% $K_2CO_3$ and 5% $Na_2S_2O_3$) and 0.1 ml of 0.3% (w/v) 3,6-dinitrophthalic acid. The reaction mixture was boiled for 10 min before the absorbance was measured at 450 nm. One unit of α-amylase was defined as the amount of activity that produces 1 μmol of reducing sugars per min at 37° C.

In the absence of the sorghum liquor waste, about 90% of the α-amylase activity remained after 10 min of treatment at 50° C., and all activity was lost at 60° C. Unexpectedly, when α-amylase was mixed with the sorghum liquor waste at a ratio of 1:10 (v/w), almost no activity was lost after 10 min treatment at 50° C. There was about 60% of activity remained after the 60 or 70° C. treatment. Little activity was detected after the 80° C. treatment.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A composition providing increased enzyme thermostability, comprising a thermolabile enzyme selected from the group consisting of phytase, cellulase, and α-amylase admixed with a sorghum liquor waste at a ratio of 1:2-10 (v/w), wherein said sorghum waste is the remains after two distillations of fermented sorghum and contains 10-13% crude starch, 14-22% crude proteins, 4-7% crude lipids, 17-21% crude fibers, and 4-46% crude ash.

2. The composition of claim 1, wherein the sorghum liquor waste is in dry form.

3. The composition of claim 2, wherein the sorghum liquor waste is grounded and sieved before it is mixed with said enzyme.

4. The composition of claim 3, wherein the liquor waste is sieved with a net having a mesh size of 0.64-cm.

5. The composition of claim 1, wherein the composition is in dry form.

6. The composition of claim 1, wherein the enzyme is cellulase.

7. The composition of claim 1, wherein the enzyme is α-amylase.

8. The composition of claim 1, wherein the enzyme is phytase.

9. A method of enhancing enzyme thermostability, the method comprising:
   mixing a solution of a thermolabile enzyme with a sorghum liquor waste at a ratio of 1:2-10, wherein said enzyme is selected from the group consisting of phytase, cellulase, and α-amylase and said sorghum waste is the remains after two distillations of fermented sorghum and contains 10-13% crude starch, 14-22% crude proteins, 4-7% crude lipids, 17-21% crude fibers, and 4-46% crude ash, and
   drying the mixture.

* * * * *